United States Patent
Laitinen et al.

(10) Patent No.: US 11,352,346 B2
(45) Date of Patent: Jun. 7, 2022

(54) PROCESS FOR THE PREPARATION OF 2-(5-METHOXYISOCHROMAN-1-YL)-4,5-DIHYDRO-1H-IMIDAZOLE AND THE HYDROGENSULFATE SALT THEREOF

(71) Applicant: ORION CORPORATION, Espoo (FI)

(72) Inventors: Ilpo Laitinen, Espoo (FI); Mikko Leskinen, Helsinki (FI); Mikko Mäkelä, Espoo (FI)

(73) Assignee: ORION CORPORATION, Espoo (FI)

( * ) Notice: Subject to any disclaimer, the term of this patent is extended or adjusted under 35 U.S.C. 154(b) by 0 days.

(21) Appl. No.: 16/768,093

(22) PCT Filed: Nov. 30, 2018

(86) PCT No.: PCT/FI2018/050864
§ 371 (c)(1),
(2) Date: May 29, 2020

(87) PCT Pub. No.: WO2019/106238
PCT Pub. Date: Jun. 6, 2019

(65) Prior Publication Data
US 2020/0308152 A1    Oct. 1, 2020

(30) Foreign Application Priority Data

Dec. 1, 2017  (FI) ..................... 20176085

(51) Int. Cl.
| | | |
|---|---|---|
| *C07D 405/04* | (2006.01) | |
| *C07D 311/76* | (2006.01) | |
| *C07F 7/10* | (2006.01) | |

(52) U.S. Cl.
CPC .......... *C07D 405/04* (2013.01); *C07D 311/76* (2013.01); *C07F 7/10* (2013.01)

(58) Field of Classification Search
CPC .................................................. C07D 405/04
See application file for complete search history.

(56) References Cited

U.S. PATENT DOCUMENTS 6,410,562 B1 * 6/2002 Jirousek ............... C07D 233/10
514/314

FOREIGN PATENT DOCUMENTS

WO    WO 2013/150173 A1    10/2013

OTHER PUBLICATIONS

Neef "One-Step Conversions of Esters to 2-Imidazolines, Benzimidazoles, and Benzothiazoles by Aluminum Organic Reagents" J. Org. Chem. 1981, 46, 2824.*

Loughlin, Wendy A., et al.: "Cyclodehydration of N-(Aminoalkyl) benzamides under Mild Conditions with a Hendrickson Reagent Analogue," *Journal of Organic Chemistry*, vol. 78, No. 14 Jun. 27, 2013, pp. 7356-7361.

Reverdito, Ana M., et al.: "Synthesis and Synthetic Applications of 1-Aryl-2-alkyl-4,5-dihydro-1H-imidazoles," *Synthetic Communications*, vol. 42, 2012, pp. 2083-2097.

International Search Report, issued by the European Patent Office for PCT/FI2018/050864, dated Feb. 12, 2019, 3 pages.

* cited by examiner

*Primary Examiner* — David K O'Dell
(74) *Attorney, Agent, or Firm* — Finnegan, Henderson, Farabow, Garrett & Dunner, LLP

(57) ABSTRACT

The present disclosure relates to an improved process for the preparation of isochroman structured alpha2A adrenoceptor agonist, namely 2-(5-methoxyisochroman-1-yl)-4,5-dihydro-1H-imidazole of formula (I) and a pharmaceutically acceptable salts thereof, such as 2-(5-methoxyisochroman-1-yl)-4,5-dihydro-1H-imidazole hydrogensulfate of formula (Ia), and to a novel intermediate compound used in the process, namely N-(2-aminoethyl)-5-methoxyisochroman-1-carboxamide monohydrate of formula (V). Alpha2A agonists are useful in the treatment of anxiety, and for use as a sedative or analgesic agent, and other diseases where alpha2A agonism is desired.

11 Claims, No Drawings

PROCESS FOR THE PREPARATION OF 2-(5-METHOXYISOCHROMAN-1-YL)-4,5-DIHYDRO-1H-IMIDAZOLE AND THE HYDROGENSULFATE SALT THEREOF

This is a National Stage Application under 35 U.S.C. § 371 of International Patent Application No. PCT/FI2018/050864, filed Nov. 30, 2018, which claims the benefit of priority of Finnish Patent Application No. 20176085, filed Dec. 1, 2017, both of which are incorporated herein by reference.

TECHNICAL FIELD

The present disclosure relates to an improved process for the preparation of isochroman structured alpha2A adrenoceptor agonist, namely 2-(5-methoxyisochroman-1-yl)-4,5-dihydro-1H-imidazole (I) and a pharmaceutically acceptable salts thereof, such as a sulfate salt (Ia), and to a novel intermediate compound used in the process, namely N-(2-aminoethyl)-5-methoxyisochroman-1-carboxamide monohydrate (V).

BACKGROUND OF THE INVENTION

The compound 2-(5-methoxyisochroman-1-yl)-4,5-dihydro-1H-imidazole of formula (I) and a pharmaceutically acceptable salts thereof have been disclosed in WO 2013/150173. Compound of formula (I) exhibits agonistic activities on adrenergic alpha2 receptors, especially on alpha2A receptor, and can thus be used in the treatment of a disorder, condition or disease where an alpha2A agonist is indicated to be useful, particularly for use as a sedative or analgesic agent, and for use in the treatment of anxiety.

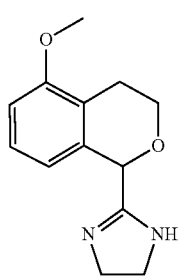

(I)

WO 2013/150173 discloses a process for the preparation of the compound of formula (I) and salts thereof through a 2-(5-bromoisochroman-1-yl)-4,5-dihydro-1H-imidazole intermediate of formula (X) as shown in scheme 1.

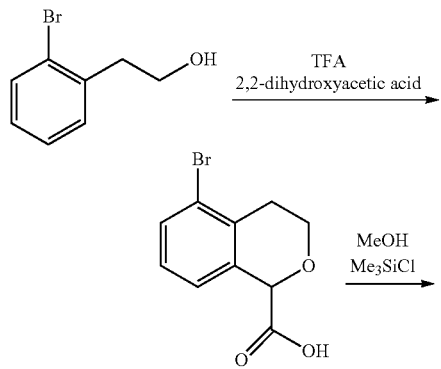

Scheme 1.

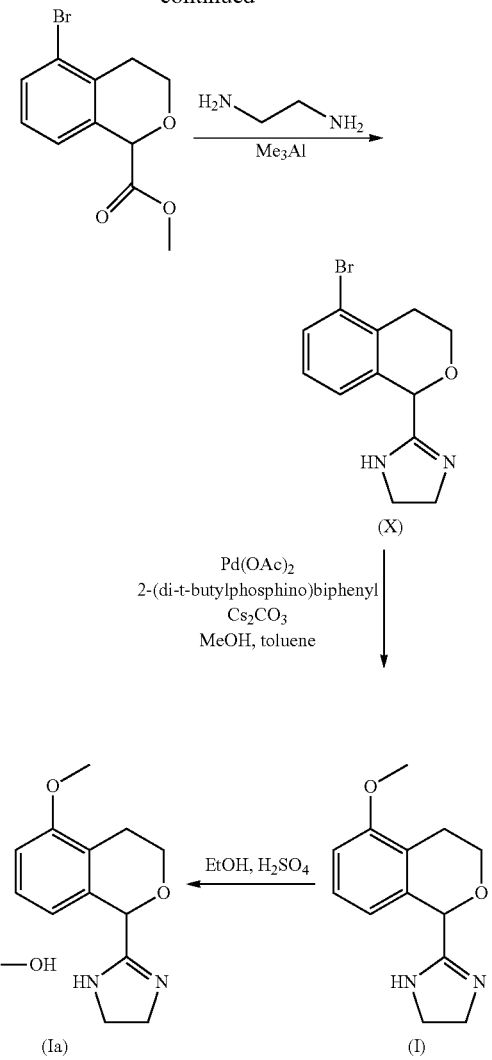

This process of scheme 1 comprises refluxing the mixture of 2-(2-bromophenyl)ethanol, TFA and 2,2-dihydroxyacetic acid to obtain 5-bromoisochroman-1-carboxylic acid which is further mixed with methanol and trimethylsilylchloride to form methyl 5-bromoisochroman-1-carboxylate. To a solution of ethylenediamine, trimethylaluminium and toluene is added the mixture of methyl 5-bromoisochroman-1-carboxylate and toluene to obtain 2-(5-bromoisochroman-1-yl)-4,5-dihydro-1H-imidazole of formula (X). Finally methanol and toluene is added to a mixture of 2-(5-bromoisochroman-1-yl)-4,5-dihydro-1H-imidazole of formula (X), 2-(di-t-butylphosphino)biphenyl, palladium(II)acetate and Cs$_2$CO$_3$, and formed 2-(5-methoxyisochroman-1-yl)-4,5-dihydro-1H-imidazole of formula (I) is isolated from the reaction mixture.

The sulfate salt (Ia) of compound of formula (I) is prepared from isolated 2-(5-methoxyisochroman-1-yl)-4,5-dihydro-1H-imidazole of formula (I) in ethanol by adding sulfuric acid in ethanol.

WO 2013/150173 discloses also another process for preparing derivatives of formula (I). In that process compound of formula (Y) is prepared through ethyl 5-methoxyisochroman-1-carboxylate intermediate of formula (IV) according to scheme 2.

Scheme 2.

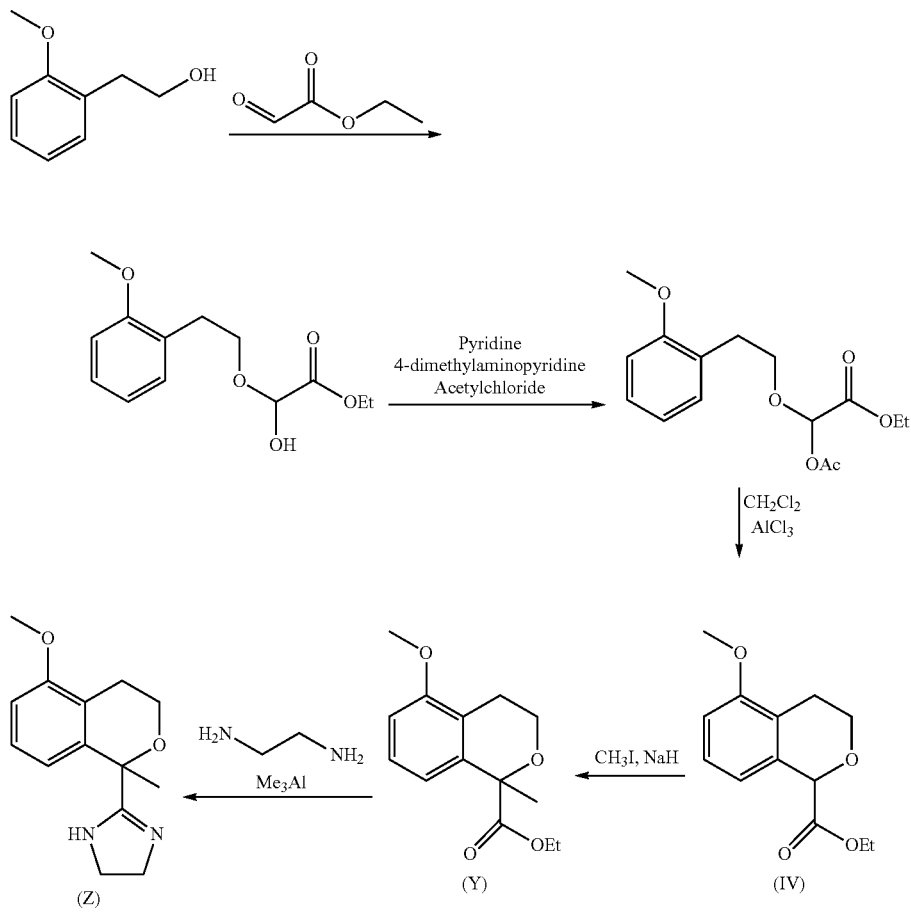

This process of scheme 2 comprises reacting 2-(2-methoxyphenyl)ethanol with ethyl 2-oxoacetate in toluene to form ethyl 2-hydroxy-2-(2-methoxyphenethoxy)acetate which is further treated with pyridine, 4-dimethylaminopyridine and acetyl chloride to form ethyl 2-acetoxy-2-(2-methoxyphenethoxy)acetate. After several purification steps the isolated ethyl 2-acetoxy-2-(2-methoxyphenethoxy)acetate is dissolved in dichloromethane and treated with AlCl₃ to form ethyl 5-methoxyisochroman-1-carboxylate of formula (IV). The intermediate compound of formula (Y) is finally reacted with ethylenediamine in the presence of trimethylaluminium and toluene to form the 4,5-dihydroimidazole compound of formula (Z).

The above mentioned processes have several drawbacks. Due to the unfavorable reagents and the complex work-ups the purity and the yield of the product are very poor. Further, trimethylaluminum is a pyrophoric reagent which limits its usefulness. Moreover, the processes are very difficult to scale-up, i.e. those may not be readily adapted for use on industrial scale.

Thus, there is a need for a more practical and economical process that is suitable for the manufacture of the compound of formula (I) and a salt thereof in high yield and purity also being feasible for use in a large scale.

SUMMARY OF THE INVENTION

It has now been found that the compound of formula (I) can be prepared using a process which is more practical and economical and suitable for use in a large industrial scale. In particular, compound of formula (I) and a sulfate salt thereof prepared by simplified procedures together with the effective purification steps can be isolated in high yield and excellent purity. Moreover, the use of pyrophoric trimethylaluminum is avoided.

Thus, an object of the present disclosure is to provide a novel process for the preparation of 2-(5-methoxyisochroman-1-yl)-4,5-dihydro-1H-imidazole of formula (I) and pharmaceutically acceptable salts thereof, such as 2-(5-methoxyisochroman-1-yl)-4,5-dihydro-1H-imidazole hydrogensulfate of formula (Ia).

Another object of the present disclosure is to provide a process for the preparation of a novel intermediate N-(2-aminoethyl)-5-methoxyisochroman-1-carboxamide monohydrate of formula (V) and a process for the preparation of 2-(5-methoxyisochroman-1-yl)-4,5-dihydro-1H-imidazole of formula (I) and a sulfate salt thereof using said intermediate of formula (V).

Another object of the present disclosure is to provide a novel intermediate N-(2-aminoethyl)-5-methoxyisochroman-1-carboxamide monohydrate of formula (V).

The process of the present disclosure can be summarized, but not limited, according to the following general reaction scheme 3 wherein, if not clearly otherwise stated, all abbreviations and expressions have the meanings well known to the person skilled in the art of organic chemistry.

Scheme 3.

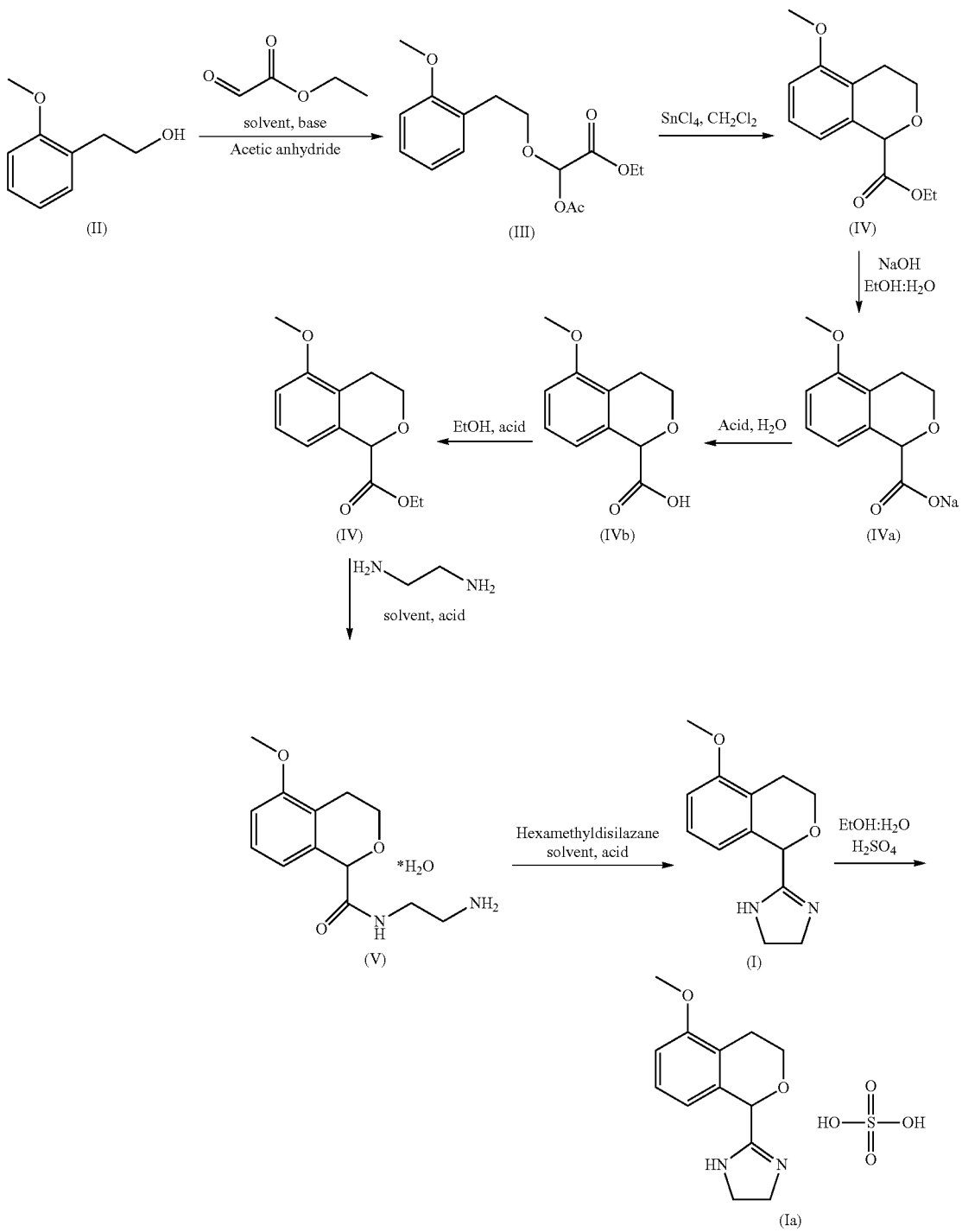

DETAILED DESCRIPTION OF THE INVENTION

The present disclosure relates to a novel process for preparation of 2-(5-methoxyisochroman-1-yl)-4,5-dihydro-1H-imidazole of formula (I) and a pharmaceutically acceptable salts thereof, such as 2-(5-methoxyisochroman-1-yl)-4,5-dihydro-1H-imidazole hydrogensulfate of formula (Ia).

In one embodiment the present disclosure relates to a process for the preparation of 2-(5-methoxyisochroman-1-yl)-4,5-dihydro-1H-imidazole of formula (I) or a pharmaceutically acceptable salt thereof

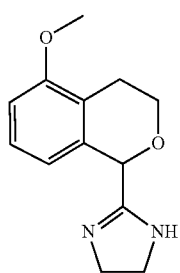

(I)

by reacting N-(2-aminoethyl)-5-methoxyisochroman-1-carboxamide monohydrate of formula (V)

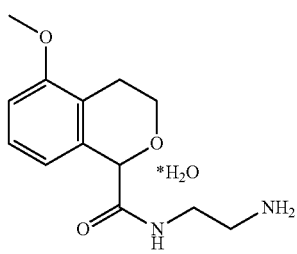

(V)

with suitable condensation reagent under acidic conditions and in the presence of a non-reactive solvent, to obtain 2-(5-methoxyisochroman-1-yl)-4,5-dihydro-1H-imidazole of formula (I), which is optionally converted to its pharmaceutically acceptable salt.

In one embodiment the present disclosure relates to above process, further comprising the step of converting the compound of formula (I) to 2-(5-methoxyisochroman-1-yl)-4,5-dihydro-1H-imidazole hydrogensulfate of formula (Ia)

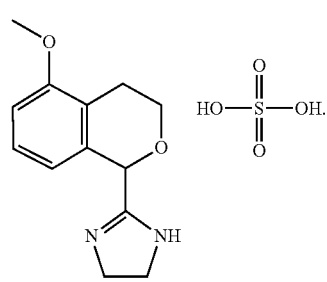

(Ia)

In one embodiment the present disclosure relates to a process for the preparation of compound of formula (I), comprising the steps of
a) reacting N-(2-aminoethyl)-5-methoxyisochroman-1-carboxamide monohydrate of formula (V) in suitable solvent, e.g. xylene, with suitable condensation reagent, e.g. hexamethyldisilazane, in the presence of catalytic amount of an acid, e.g. sulphuric acid; and
b) without isolating the formed 2-(5-methoxyisochroman-1-yl)-4,5-dihydro-1H-imidazole of formula (I) from the reaction mixture, converting said 2-(5-methoxyisochroman-1-yl)-4,5-dihydro-1H-imidazole to 2-(5-methoxyisochroman-1-yl)-4,5-dihydro-1H-imidazole hydrogensulfate of formula (Ia).

In one embodiment the present disclosure relates to above process wherein, the step b) is carried out by treating the reaction mixture with ethanol-water solution and adding sulfuric acid.

In one embodiment the present disclosure relates to a process for the preparation of compound of formula (I), comprising the steps of
a) reacting N-(2-aminoethyl)-5-methoxyisochroman-1-carboxamide monohydrate of formula (V) in xylene with hexamethyldisilazane at an elevated temperature, e.g. above 80° C., in the presence of catalytic amount of sulphuric acid to obtain 2-(5-methoxyisochroman-1-yl)-4,5-dihydro-1H-imidazole of formula (I);
b) without isolating the formed 2-(5-methoxyisochroman-1-yl)-4,5-dihydro-1H-imidazole of formula (I) adding water and HCl to the reaction mixture to convert the compound of formula (I) to its hydrochloride salt;
c) isolating the water phase;
d) adding suitable extraction solvent, e.g. methylene chloride, and an inorganic base, e.g. NaOH;
e) isolating the organic phase;
f) adding ethanol-water solution and sulphuric acid to form 2-(5-methoxyisochroman-1-yl)-4,5-dihydro-1H-imidazole hydrogensulfate of formula (Ia);
g) distilling the solvent off;
h) adding ethanol to the ethanol-water solution;
i) crystallizing 2-(5-methoxyisochroman-1-yl)-4,5-dihydro-1H-imidazole hydrogensulfate of formula (Ia) by cooling and optionally seeding; and
j) isolating the crystalline compound of formula (Ia).

In one embodiment the present disclosure relates to process for the preparation of N-(2-aminoethyl)-5-methoxyisochroman-1-carboxamide monohydrate of formula (V).

In one embodiment the present disclosure relates to a process for the preparation of N-(2-aminoethyl)-5-methoxyisochroman-1-carboxamide monohydrate of formula (V)

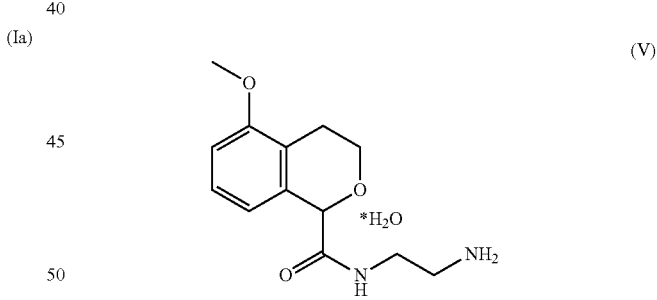

(V)

comprising the steps of
a) reacting 2-(2-methoxyphenyl)ethanol of formula (II)

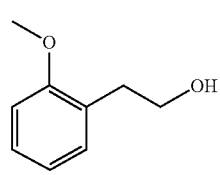

(II)

with ethyl 2-oxoacetate in suitable organic solvent, e.g. dichloromethane or toluene, and the presence of a tertiary aliphatic amine, e.g. trimethylamine or triethylamine, and subsequently adding acetic anhydride to the reaction mixture to form ethyl 2-acetoxy-2-(2-methoxyphenethoxy)acetate of formula (III);

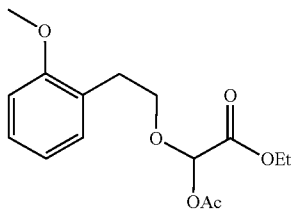
(III)

b) adding ethyl 2-acetoxy-2-(2-methoxyphenethoxy)acetate of formula (III) to the mixture of tin tetrachloride and chlorinated hydrocarbon solvent, e.g. dichloromethane, to form ethyl 5-methoxyisochroman-1-carboxylate of formula (IV); and

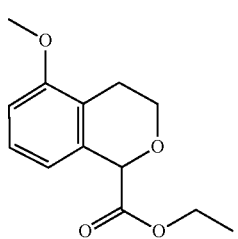
(IV)

c) reacting the ethyl 5-methoxyisochroman-1-carboxylate of formula (IV) with ethylene diamine in suitable solvent, e.g. aliphatic or aromatic hydrocarbon solvent, such as toluene, and the presence of a catalytic amount of suitable acid, e.g. acetic acid, to form N-(2-aminoethyl)-5-methoxyisochroman-1-carboxamide monohydrate of formula (V).

In one embodiment the present disclosure relates to a process for the preparation of N-(2-aminoethyl)-5-methoxyisochroman-1-carboxamide monohydrate of formula (V), comprising the steps of a) reacting 2-(2-methoxyphenyl)ethanol of formula (II)

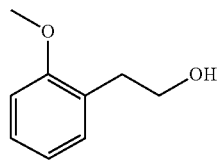
(II)

with ethyl 2-oxoacetate in suitable solvent, e.g. dichloromethane, and the presence of a tertiary aliphatic amine, e.g. trimethylamine or trimethylamine, and subsequently adding acetic anhydride to the reaction mixture to form ethyl 2-acetoxy-2-(2-methoxyphenethoxy)-acetate of formula (III);

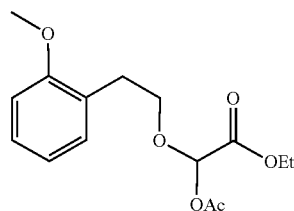
(III)

b) adding ethyl 2-acetoxy-2-(2-methoxyphenethoxy)acetate of formula (III) to the mixture of tin tetrachloride and a chlorinated hydrocarbon solvent to form ethyl 5-methoxyisochroman-1-carboxylate of formula (IV);

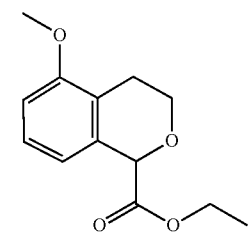
(IV)

c) without isolating the formed ethyl 5-methoxyisochroman-1-carboxylate of formula (IV) adding water, NaOH and ethanol to the reaction mixture to obtain sodium 5-methoxyisochroman-1-carboxylate of formula (IVa);

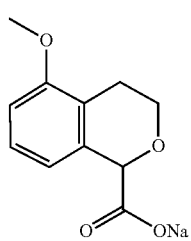
(IVa)

d) treating the sodium 5-methoxyisochroman-1-carboxylate of formula (IVa) with suitable acid, e.g. strong organic or inorganic acid, such as HCl, in water and isolating the formed 5-methoxyisochroman-1-carboxylic acid of formula (IVb);

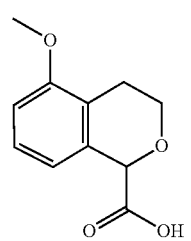
(IVb)

e) reacting the 5-methoxyisochroman-1-carboxylic acid of formula (IVb) in suitable organic solvent, e.g. toluene, with ethanol in the presence of suitable acid, e.g. HCl, to form ethyl 5-methoxyisochroman-1-carboxylate of formula (IV); and

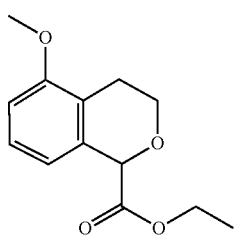
(IV)

f) reacting the ethyl 5-methoxyisochroman-1-carboxylate of formula (IV) with ethylene diamine in aliphatic or aromatic hydrocarbon solvent and the presence of a catalytic amount of suitable acid, e.g. acetic acid, to form N-(2-aminoethyl)-5-methoxyisochroman-1-carboxamide monohydrate of formula (V).

In one embodiment the present disclosure relates to a process for the preparation of N-(2-aminoethyl)-5-methoxyisochroman-1-carboxamide monohydrate of formula (V), comprising the steps of a) reacting 2-(2-methoxyphenyl)ethanol of formula (II) with ethyl 2-oxoacetate in toluene and the presence of trimethylamine and subsequently adding acetic anhydride to the reaction mixture to form ethyl 2-acetoxy-2-(2-methoxyphenethoxy)acetate of formula (III);

b) adding ethyl 2-acetoxy-2-(2-methoxyphenethoxy)acetate of formula (III) in dichloromethane to the mixture of tin tetrachloride and dichloromethane to form ethyl 5-methoxyisochroman-1-carboxylate of formula (IV);

c) without isolating the formed ethyl 5-methoxyisochroman-1-carboxylate of formula (IV) from the reaction mixture adding water, NaOH and ethanol to the reaction mixture to obtain sodium 5-methoxyisochroman-1-carboxylate of formula (IVa);

d) treating the sodium 5-methoxyisochroman-1-carboxylate of formula (IVa) with HCl in water and isolating the formed 5-methoxyisochroman-1-carboxylic acid of formula (IVb);

e) reacting 5-methoxyisochroman-1-carboxylic acid of formula (IVb) in toluene with ethanol in the presence of HCl to form ethyl 5-methoxyisochroman-1-carboxylate of formula (IV) in toluene solution; and f) reacting the ethyl 5-methoxyisochroman-1-carboxylate toluene solution obtained from step e) with ethylene diamine in the presence of a catalytic amount of acetic acid to form N-(2-aminoethyl)-5-methoxyisochroman-1-carboxamide monohydrate of formula (V).

In one embodiment the present disclosure relates to a process for the preparation N-(2-aminoethyl)-5-methoxyisochroman-1-carboxamide monohydrate of formula (V) according to the above processes further comprising the steps of g) extracting the reaction mixture by adding water immiscible organic solvent, e.g. toluene, and water and subsequently gradually adding suitable acid, e.g. acetic acid; and h) crystallizing N-(2-aminoethyl)-5-methoxyisochroman-1-carboxamide monohydrate of formula (V) from the water phase by adding a suitable strong base, e.g. NaOH.

In one embodiment the present disclosure relates to a process for the preparation of 2-(5-methoxyisochroman-1-yl)-4,5-dihydro-1H-imidazole of formula (I) or a pharmaceutically acceptable salt thereof comprising the steps of a) reacting 2-(2-methoxyphenyl)ethanol of formula (II) with ethyl 2-oxoacetate in suitable solvent and the presence of an organic base and subsequently adding acetic anhydride to the reaction mixture to form ethyl 2-acetoxy-2-(2-methoxyphenethoxy)acetate of formula (III);

b) adding ethyl 2-acetoxy-2-(2-methoxyphenethoxy)acetate of formula (III) to the mixture of tin tetrachloride and a chlorinated hydrocarbon solvent to form ethyl 5-methoxyisochroman-1-carboxylate of formula (IV);

c) reacting the ethyl 5-methoxyisochroman-1-carboxylate of formula (IV) with ethylene diamine in aliphatic or aromatic hydrocarbon solvent and the presence of a catalytic amount of acid to form N-(2-aminoethyl)-5-methoxyisochroman-1-carboxamide monohydrate of formula (V);

d) reacting N-(2-aminoethyl)-5-methoxyisochroman-1-carboxamide monohydrate of formula (V) in suitable solvent with hexamethyldisilazane in the presence of catalytic amount of an acid; and e) without isolating the formed 2-(5-methoxyisochroman-1-yl)-4,5-dihydro-1H-imidazole of formula (I) from the reaction mixture, converting said 2-(5-methoxyisochroman-1-yl)-4,5-dihydro-1H-imidazole to 2-(5-methoxyisochroman-1-yl)-4,5-dihydro-1H-imidazole hydrogensulfate of formula (Ia).

In one embodiment the present disclosure relates to use of a compound of formula (V) in the preparation of the compound of formula (I) or a pharmaceutically acceptable salts thereof, such as a sulfate salt.

In one embodiment the present disclosure relates to use of a compound of formula (V) in the preparation of the compound of formula (I) or a pharmaceutically acceptable salts thereof, such as sulfate salt, wherein the compound of formula (V) is prepared according to the method disclosed above.

In one embodiment the present disclosure relates to a novel compound of formula (V).

In one embodiment the present disclosure relates to the compound of formula (V), which is used as an intermediate for preparing compound of formula (I) or (Ia).

It was found that the compound of formula (I) and a sulfate salt thereof prepared according to the process described herein, can be obtained in high yield and excellent purity. Also the process for the preparation of compound of formula (V), as described herein, is very effective leading to high yield and is suitable for use in an industrial scale. The quality of the isolated compound of formula (V) is excellent. It is well characterized crystalline compound.

The conversion of the compound of formula (II) to the compound of formula (III) involves a presence of a base. It was found that by changing the base from pyridine to a tertiary aliphatic amine, such as trimethylamine, the extra purification steps can be avoided.

It was also found that when converting the compound of formula (III) to the compound of formula (IV) changing the addition order of reagents and using $SnCl_4$ instead of $AlCl_3$ reduces the formation of impurities. Moreover, the purification of compound of formula (IV) can be carried out via its sodium salt of formula (IVa) instead of using many distillations to dryness which is a difficult operation to handle in a large scale. In addition, this purification method is more effective.

It was found that the conversion of the compound of formula (IV) to the compound of formula (I) can be carried out by safer two-step method. This new method avoids the use of pyrophoric $AlMe_3$ and the work-up and isolation of the new intermediate compound of formula (V) removes impurities effectively.

It was found that the conversion of the compound of formula (V) to the sulfate salt (Ia) of formula (I) is possible to carry out without isolation of the compound of formula (I).

The starting materials, such as compound of formula (II), are commercially available or can be prepared according to the methods known in the art.

The present disclosure will be explained in more detailed by the following examples. The examples are meant for illustrating purposes only and do not limit the scope of the invention defined in the claims.

Example 1: Preparation of ethyl 2-acetoxy-2-(2-methoxyphenethoxy)acetate (III)

A flask inserted with $N_2$ was charged with dichloromethane (900 mL) followed by 2-(2-methoxyphenyl)ethanol (II) (150 g, 1.0 equivalent). Then ethyl 2-oxoacetate in toluene (50%, 191 g, 0.95 equivalent) and trimethylamine (199 g, 2.0 equivalent) were subsequently added and the reaction mixture was stirred 1 hour. The bath temperature was adjusted to 0° C. and acetic anhydride (161 g, 1.6 equivalent) was added to the reaction mixture. The reaction mass was stirred 1 h at 0±5° C. The reaction mixture was stirred 2 hours at 20-30° C.

Water (450 mL) was added to the reaction mixture. The reaction mixture was stirred 10 min and the organic layer was separated. Water (450 mL) and HCl (25 mL, 30% aq, 0.24 equivalent) were added to the reaction mixture. The reaction mixture was stirred 10 min and the organic layer was separated. Water (450 mL) was added to the reaction mixture. The reaction mixture was stirred 10 min and the organic layer was separated.

The product was collected by distilling off the organic layer until the reaction mass reached 105-110° C. The reaction mixture was cooled to 30-50° C. and the organic layer was distilled off at reduced pressure (100 mbar) until the reaction mass reached 100° C. The distill residue was the product and it was yellowish oil at 87.0 HPLC a-% purity.

Example 2: Preparation of sodium 5-methoxyisochroman-1-carboxylate (IVa)

A flask inserted with $N_2$ was charged with dichloromethane (600 mL) followed by tin(IV) chloride (63 mL, 1.3 equivalent). The reaction mixture was cooled to 0±3° C. and ethyl 2-acetoxy-2-(2-methoxyphenethoxy)acetate (120 g, 1 equivalent) in dichloromethane (840 mL) was added to the reaction mixture at 0±3° C. over 1 hour. The reaction mixture was stirred 1 hour at 0±3° C. and water (360 mL) was added to the reaction mixture at 0±3° C. The reaction mixture was stirred 10 min and the organic layer was separated. The organic layer was washed with water (360 mL). Ethanol (360 mL) was added to the reaction mixture. The organic layer was distilled off until the reaction mass reached 60° C. (distillation residue 360 mL).

Water (192 mL) was added to the reaction and the reaction mixture was heated to 50±3° C. NaOH (50%, 39 mL, 1.8 equivalents) was added over 35 minutes and the temperature is maintained at 50±3° C. during the addition. After the addition, the reaction mass was seeded with crystalline sodium 5-methoxyisochroman-1-carboxylate (100 mg). Ethanol (276 mL) was added over 50 minutes and the temperature is maintained at 50±3° C. during the addition. The reaction mass was stirred 1 hour at 50±3° C. and cooled to 0° C. over 3 hours.

After stirring for 60 min at 0° C. the product was collected by filtration and the cake was washed with tert-butylmethyl ether (96 mL). The product was dried in a vacuum oven at 60° C. to give 75.7 g (80.9%) of white solid at 99.2 HPLC a-% purity.

Example 3: Preparation of 5-methoxyisochroman-1-carboxylic acid (IVb)

A flask inserted with $N_2$ was charged with water (1200 mL), ethanol (121 mL) and hydrogen chloride (30%, 103 mL, 1.3 equivalents). Sodium 5-methoxyisochroman-1-carboxylate (173 g, 1 equivalents) was added to the reaction mixture at 20±5° C. followed by water (173 mL). The reaction mass was stirred 7 hour at 20±3° C. The reaction mass was cooled to 0±3° C. over 5 hours and stirred 8 hours at 0±3° C.

The product was collected by filtration and the cake was washed with water (173 mL). The product was dried in a vacuum oven at 60° C. to give 148.2 g (94.7%) of white solid at 99.6 HPLC a-% purity.

Example 4: Preparation of ethyl 5-methoxyisochroman-1-carboxylate (IV)

5-Methoxyisochroman-1-carboxylic acid (13.2 g), ethanol (80 ml) and toluene (70 ml) were charged. The mixture was warmed to 60±5° C. HCl in ethanol 20% (7.9 ml) was added. The mixture was stirred for 3 hours at 60±5° C. About 80 ml was distilled off under normal pressure. The mixture was cooled to room temperature. Water (50 ml) was added and the mixture was stirred for a few minutes. The phases were allowed to separate and the water phase was separated off. About 30 ml was distilled off under normal pressure. The toluene solution was used as such for the next stage. The yield is practically quantitative. HPLC-purity (toluene excluded) was 99.0%.

Example 5: Preparation of N-(2-aminoethyl)-5-methoxyisochroman-1-carboxamide monohydrate (V)

Ethyl 5-methoxyisochroman-1-carboxylate toluene solution from example 4 and ethylene diamine (13.0 ml) were charged. Acetic acid (0.30 ml) was added. The mixture was warmed to 97±3° C. The mixture was stirred for 5 hours at 97±3° C. The mixture was cooled to 10-20° C. Toluene (70 ml) and water (110 ml) were added at 10-20° C. Acetic acid (19 ml) was added gradually at 10-20° C. The mixture was heated to 80±3° C. and stirred for 0.5 hour at 80±3° C. Phases were allowed to separate and the toluene phase was separated off. 50% NaOH (21 ml) was added slowly at 45±5° C. The mixture was cooled slowly (2-3 hours) to 10±5° C. and stirred for about 2 hours at 10±5° C. The crystalline compound was filtered and washed with water (2*20 ml). The compound was dried under reduced pressure at 20±5° C. The yield was 14.0 g (82%). The HPLC-purity was 99.5%.

$^1$H-NMR (CDCl$_3$): 1.55 ppm 4H (s broad), 2.75-2.85 ppm 4H (m), 3.20-3.30 1H (m), 3.32-3.42 ppm 1H (m), 3.77-3.86 ppm 4H (m+s), 4.20-4.28 ppm 1H (m), 5.17 ppm 1H (s), 6.76 ppm 1H (d), 6.94 ppm 1H (s), 7.17 ppm 1H (tr), 7.33 ppm 1H (d).

$^{13}$C-NMR: 22.8, 41.5, 41.9, 55.4, 63.9, 77 (under CDCl$_3$), 108.5, 117.8, 121.9, 126.7, 133.3, 156.6, 171.0.

Example 6: 2-(5-methoxyisochroman-1-yl)-4,5-dihydro-1H-imidazole hydrogensulfate (Ia)

N-(2-aminoethyl)-5-methoxyisochroman-1-carboxamide monohydrate (12 g) and xylene (60 ml) were charged. Sulfuric acid 93% (0.3 ml) was added. Hexamethyldisilazane (26 ml) was added. The mixture was heated to 122° C. and stirred for 4 hours at 122±3° C. The mixture was cooled. Water (60 ml) and 30% HCl (14 ml) were added slowly at 40±5° C. The mixture was heated to 60±3° C. and stirred for 2 hours at 60±3° C. The phases were allowed to separate and the organic phase was separated off. Methylene chloride (80 ml) was added to the water phase. 50% NaOH (14 ml) was added gradually at 20±5° C. The phases were allowed to separate. The water phase was separated off. Water (30 ml) was added to the organic phase. The mixture was stirred for a few minutes. The phases were allowed to separate. The water phase was separated off. Ethanol (80 ml), water (15 ml) and sulfuric acid 93% (2.4 ml) were added to the methylene chloride solution. Methylene chloride was distilled off under normal pressure. The ethanol-water solution was cooled to 70±5° C. and ethanol (42 ml) was added. The solution was cooled to room temperature. Seed crystals were added during the cooling. The mixture was stirred overnight at room temperature. The mixture was cooled to 0-5° C. and stirred about 4 hours at 0-5° C. The crystalline compound was filtered and washed with cold ethanol (20 ml). The product was dried under reduced pressure at 60-70° C. The yield was 11.07 g (74.9%). The HPLC-purity was 99.9%.

$^1$H-NMR (DMSO-$d_6$): 2.6-2.8 ppm 2H (m), 3.82 ppm 3H (s), 3.89 ppm 4H (s), 3.8-3.9 ppm 1H (m), 4.1-4.2 ppm 1H (m), 5.78 ppm 1H (s), 6.82 ppm 1H (d), 6.99 ppm 1H (d), 7.28 ppm 1H (tr), 9.1-10.8 ppm 3H (s+s, broad).

$^{13}$C-NMR: 22.2, 44.8, 55.9, 63.6, 69.6, 110.4, 117.1, 122.7, 127.8, 130.9, 157.0, 169.8.

A person skilled in the art will appreciate that the embodiments described herein can be modified without departing from the inventive concept. A person skilled in the art also understands that the present disclosure is not limited to the particular embodiments disclosed but is intended to also cover modifications of the embodiments that are within the scope of the present disclosure.

The invention claimed is:

1. A process for the preparation of 2-(5-methoxyisochroman-1-yl)-4,5-dihydro-1H-imidazole of formula (I) or a pharmaceutically acceptable salt thereof:

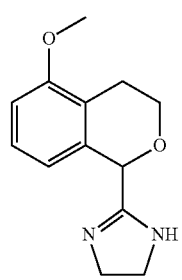

(I)

comprising:
reacting N-(2-aminoethyl)-5-methoxyisochroman-1-carboxamide monohydrate of formula (V):

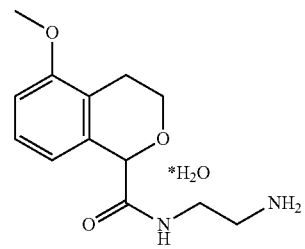

(V)

with hexamethyldisilazane under acidic conditions and in the presence of a non-reactive solvent, to obtain 2-(5-methoxyisochroman-1-yl)-4,5-dihydro-1H-imidazole of formula (I), which is optionally converted to its pharmaceutically acceptable salt.

2. The process according to claim 1, further comprising the step of converting the compound of formula (I) to 2-(5-methoxyisochroman-1-yl)-4,5-dihydro-1H-imidazole hydrogensulfate of formula (Ia):

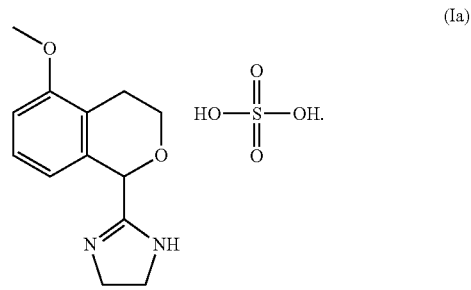

(Ia)

3. The process according to claim 1, comprising the steps of:
a) reacting N-(2-aminoethyl)-5-methoxyisochroman-1-carboxamide monohydrate of formula (V) in a suitable solvent with hexamethyldisilazane in the presence of a catalytic amount of an acid; and
b) without isolating the formed 2-(5-methoxyisochroman-1-yl)-4,5-dihydro-1H-imidazole of formula (I) from the reaction mixture, converting the 2-(5-methoxyisochroman-1-yl)-4,5-dihydro-1H-imidazole to 2-(5-methoxyisochroman-1-yl)-4,5-dihydro-1H-imidazole hydrogensulfate of formula (Ia).

4. The process according to claim 3, wherein step b) is carried out by treating the reaction mixture with ethanol-water solution and adding sulfuric acid.

5. The process according to claim 1, comprising the steps of:
a) reacting N-(2-aminoethyl)-5-methoxyisochroman-1-carboxamide monohydrate of formula (V) in xylene with hexamethyldisilazane at an elevated temperature in the presence of a catalytic amount of sulphuric acid to obtain 2-(5-methoxyisochroman-1-yl)-4,5-dihydro-1H-imidazole of formula (I);
b) without isolating the formed 2-(5-methoxyisochroman-1-yl)-4,5-dihydro-1H-imidazole of formula (I), adding water and HCl to the reaction mixture to convert the compound of formula (I) to its hydrochloride salt;
c) isolating the water phase;
d) adding suitable extraction solvent and an inorganic base;
e) isolating the organic phase;

f) adding ethanol-water solution and sulphuric acid to form 2-(5-methoxyisochroman-1-yl)-4,5-dihydro-1H-imidazole hydrogensulfate of formula (Ia);

g) distilling the solvent off;

h) adding ethanol to the ethanol-water solution;

i) crystallizing 2-(5-methoxyisochroman-1-yl)-4,5-dihydro-1H-imidazole hydrogensulfate of formula (Ia) by cooling and optionally seeding; and j) isolating the crystalline compound of formula (Ia).

6. A process for the preparation of N-(2-aminoethyl)-5-methoxyisochroman-1-carboxamide monohydrate of formula (V):

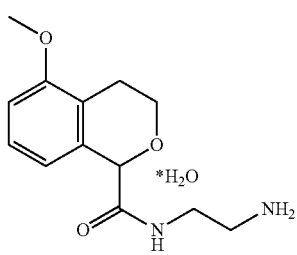

(V)

comprising the steps of:

a) reacting 2-(2-methoxyphenyl)ethanol of formula (II):

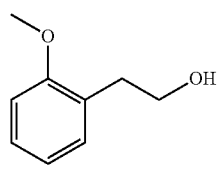

(II)

with ethyl 2-oxoacetate in a suitable solvent and in the presence of a tertiary aliphatic amine and subsequently adding acetic anhydride to the reaction mixture to form ethyl 2-acetoxy-2-(2-methoxyphenethoxy)acetate of formula (III):

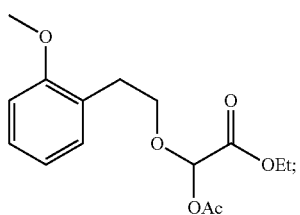

(III)

b) adding ethyl 2-acetoxy-2-(2-methoxyphenethoxy)acetate of formula (III) to the mixture of tin tetrachloride and a chlorinated hydrocarbon solvent to form ethyl 5-methoxyisochroman-1-carboxylate of formula (IV)

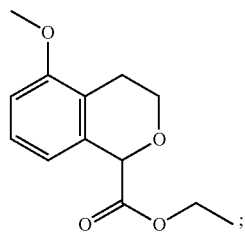

(IV)

and c) reacting the ethyl 5-methoxyisochroman-1-carboxylate of formula (IV) with ethylene diamine in aliphatic or aromatic hydrocarbon solvent and in the presence of a catalytic amount of acid to form N-(2-aminoethyl)-5-methoxyisochroman-1-carboxamide monohydrate of formula (V).

7. The process according to claim 6, comprising the steps of:

a) reacting 2-(2-methoxyphenyl)ethanol of formula (II):

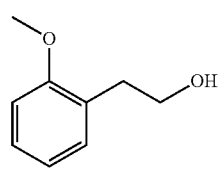

(II)

with ethyl 2-oxoacetate in a suitable solvent and in the presence of a tertiary aliphatic amine, and subsequently adding acetic anhydride to the reaction mixture to form ethyl 2-acetoxy-2-(2-methoxyphenethoxy)acetate of formula (III):

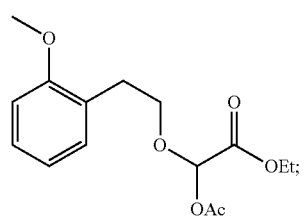

(III)

b) adding ethyl 2-acetoxy-2-(2-methoxyphenethoxy)acetate of formula (III) to the mixture of tin tetrachloride and a chlorinated hydrocarbon solvent to form ethyl 5-methoxyisochroman-1-carboxylate of formula (IV):

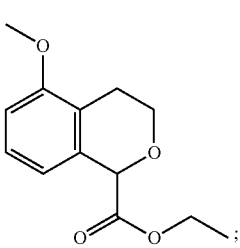

(IV)

c) without isolating the formed ethyl 5-methoxyisochroman-1-carboxylate of formula (IV), adding water, NaOH and ethanol to the reaction mixture to obtain sodium 5-methoxyisochroman-1-carboxylate of formula (IVa):

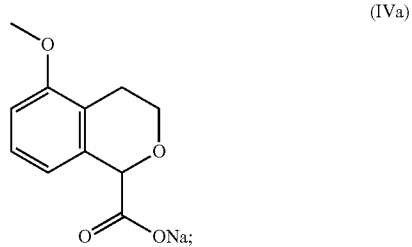

(IVa)

d) treating the sodium 5-methoxyisochroman-1-carboxylate of formula (IVa) with suitable acid in water and isolating the formed 5-methoxyisochroman-1-carboxylic acid of formula (IVb):

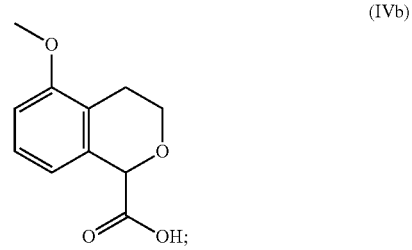

(IVb)

e) reacting the 5-methoxyisochroman-1-carboxylic acid of formula (IVb) in suitable organic solvent with ethanol in the presence of suitable acid to form ethyl 5-methoxyisochroman-1-carboxylate of formula (IV):

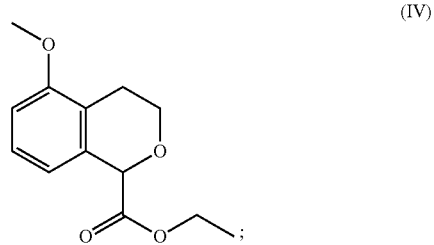 [SMILES: CCOC(=O)C1OCCc2c(OC)cccc21]

(IV)

and f) reacting the ethyl 5-methoxyisochroman-1-carboxylate of formula (IV) with ethylene diamine in aliphatic or aromatic hydrocarbon solvent and in the presence of a catalytic amount of acid to form N-(2-aminoethyl)-5-methoxyisochroman-1-carboxamide monohydrate of formula (V).

8. The process according to claim 7, comprising the steps of:

a) reacting 2-(2-methoxyphenyl)ethanol of formula (II) with ethyl 2-oxoacetate in toluene and in the presence of trimethylamine, and subsequently adding acetic anhydride to the reaction mixture to form ethyl 2-acetoxy-2-(2-methoxyphenethoxy)acetate of formula (III);

b) adding ethyl 2-acetoxy-2-(2-methoxyphenethoxy)acetate of formula (III) in dichloromethane to the mixture of tin tetrachloride and dichloromethane to form ethyl 5-methoxyisochroman-1-carboxylate of formula (IV);

c) without isolating the formed ethyl 5-methoxyisochroman-1-carboxylate of formula (IV) from the reaction mixture, adding water, NaOH and ethanol to the reaction mixture to obtain sodium 5-methoxyisochroman-1-carboxylate of formula (IVa);

d) treating the sodium 5-methoxyisochroman-1-carboxylate of formula (IVa) with HCl in water, and isolating the formed 5-methoxyisochroman-1-carboxylic acid of formula (IVb);

e) reacting 5-methoxyisochroman-1-carboxylic acid of formula (IVb) in toluene with ethanol in the presence of HCl to form ethyl 5-methoxyisochroman-1-carboxylate of formula (IV) in toluene solution; and f) reacting the ethyl 5-methoxyisochroman-1-carboxylate toluene solution obtained from step e) with ethylene diamine in the presence of a catalytic amount of acetic acid to form N-(2-aminoethyl)-5-methoxyisochroman-1-carboxamide monohydrate of formula (V).

9. The process according to claim 8 further comprising the steps of:

g) extracting the reaction mixture by adding a water immiscible organic solvent and water and subsequently gradually adding a suitable acid; and h) crystallizing N-(2-aminoethyl)-5-methoxyisochroman-1-carboxamide monohydrate of formula (V) from the water phase by adding a suitable strong base.

10. The process according to claim 1, wherein the compound of formula (V) is prepared by a process comprising the steps of:

a) reacting 2-(2-methoxyphenyl)ethanol of formula (II):

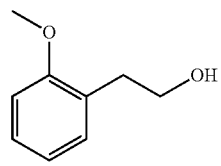

(II)

with ethyl 2-oxoacetate in a suitable solvent and in the presence of a tertiary aliphatic amine and subsequently adding acetic anhydride to the reaction mixture to form ethyl 2-acetoxy-2-(2-methoxyphenethoxy)acetate of formula (III):

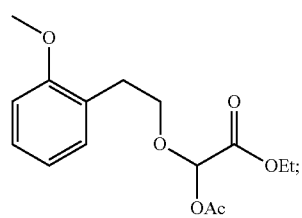

(III)

b) adding ethyl 2-acetoxy-2-(2-methoxyphenethoxy)acetate of formula (III) to the mixture of tin tetrachloride and a chlorinated hydrocarbon solvent to form ethyl 5-methoxyisochroman-1-carboxylate of formula (IV)

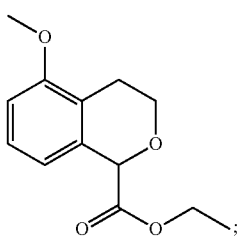
and
c) reacting the ethyl 5-methoxyisochroman-1-carboxylate of formula (IV) with ethylene diamine in aliphatic or aromatic hydrocarbon solvent and in the presence of a catalytic amount of acid to form N-(2-aminoethyl)-5-methoxyisochroman-1-carboxamide monohydrate of formula (V).
11. A compound of formula (V):
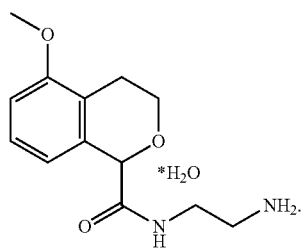
* * * * *